US010265019B2

(12) United States Patent
Gertsch et al.

(10) Patent No.: US 10,265,019 B2
(45) Date of Patent: Apr. 23, 2019

(54) ELECTRONIC HEADWEAR

(71) Applicant: TRI-MATE PRO, INC., San Diego, CA (US)

(72) Inventors: Bruce Gertsch, San Diego, CA (US); Ronald Gertsch, San Diego, CA (US); Paul Nysen, Bonsall, CA (US); Peter Nysen, San Jose, CA (US); William Swanson, San Diego, CA (US); Christopher L. Gehrisch, Vista, CA (US); Martin D. McCune, San Diego, CA (US); David L. Williams, San Diego, CA (US)

(73) Assignee: Oxystrap Int'l, Inc., San Diego, CA (US)

( * ) Notice: Subject to any disclaimer, the term of this patent is extended or adjusted under 35 U.S.C. 154(b) by 411 days.

(21) Appl. No.: 13/853,526

(22) Filed: Mar. 29, 2013

(65) Prior Publication Data

US 2014/0296669 A1    Oct. 2, 2014

(51) Int. Cl.
| | |
|---|---|
| *A61B 5/1455* | (2006.01) |
| *A61B 5/00* | (2006.01) |
| *A61B 5/0205* | (2006.01) |
| *A61B 5/01* | (2006.01) |
| A61B 5/024 | (2006.01) |

(52) U.S. Cl.
CPC .......... *A61B 5/6803* (2013.01); *A61B 5/0008* (2013.01); *A61B 5/01* (2013.01); *A61B 5/02055* (2013.01); *A61B 5/14552* (2013.01); *A61B 5/02427* (2013.01)

(58) Field of Classification Search
CPC .................................................. A61B 5/1455
See application file for complete search history.

(56) References Cited

U.S. PATENT DOCUMENTS

| | | | |
|---|---|---|---|
| 5,782,757 | A | 7/1998 | Diab et al. |
| 6,256,523 | B1 | 7/2001 | Diab et al. |
| 6,567,991 | B1 | 5/2003 | Holslag et al. |
| 6,792,300 | B1 | 9/2004 | Diab et al. |
| 6,813,511 | B2 | 11/2004 | Diab et al. |
| 6,941,162 | B2 | 9/2005 | Fudge et al. |
| 7,272,425 | B2 | 9/2007 | Al-Ali |
| 7,289,837 | B2 | 10/2007 | Mannheimer et al. |
| 7,477,924 | B2 * | 1/2009 | Chin .................. A61B 5/02411 600/323 |
| 7,483,730 | B2 | 1/2009 | Diab et al. |
| 7,574,245 | B2 | 8/2009 | Arizaga Ballesteros |
| 7,676,253 | B2 | 3/2010 | Raridan, Jr. |
| 7,698,909 | B2 | 4/2010 | Hannula et al. |
| 7,809,420 | B2 | 10/2010 | Hannula et al. |

(Continued)

FOREIGN PATENT DOCUMENTS

WO    WO-2007/050269    5/2007

*Primary Examiner* — Eric Winakur
*Assistant Examiner* — Marjan Fardanesh
(74) *Attorney, Agent, or Firm* — Tsircou Law, P.C.

(57) ABSTRACT

A headwear assembly is provided that measures physiological changes, e.g., oxygen saturation, pulse, blood pressure, and body temperature of a user during physical exercise, to include athletic activities and other situations. The headwear assembly can provide integrated functionality with an external device such as a smart phone. The headwear assembly can be embodied in various configurations, e.g., stand-alone headband, cap, visor, or a helmet.

18 Claims, 7 Drawing Sheets

(56) References Cited

U.S. PATENT DOCUMENTS

| | | |
|---|---|---|
| 7,810,359 B2 | 10/2010 | Hannula et al. |
| 7,822,453 B2 | 10/2010 | Mannheimer et al. |
| RE41,912 E | 11/2010 | Parker |
| 7,877,126 B2 | 1/2011 | Hannula et al. |
| 7,877,127 B2 | 1/2011 | Hannula et al. |
| 7,899,509 B2 | 3/2011 | Mannheimer et al. |
| 7,937,128 B2 | 5/2011 | Al-Ali |
| 7,979,102 B2 | 7/2011 | Hannula et al. |
| 8,000,761 B2 | 8/2011 | Al-Ali |
| 8,190,225 B2 | 5/2012 | Hoarau |
| 8,195,264 B2 | 6/2012 | Hoarau |
| 2005/0280531 A1 | 12/2005 | Fadem |
| 2009/0054751 A1 | 2/2009 | Babashan |
| 2010/0076276 A1* | 3/2010 | Gilland .................... 600/301 |
| 2010/0076337 A1 | 3/2010 | Medina |
| 2011/0028814 A1 | 2/2011 | Petersen et al. |
| 2011/0251469 A1 | 10/2011 | Varadan |
| 2012/0083673 A1 | 4/2012 | Al-Ali |
| 2012/0123278 A1 | 5/2012 | Diab et al. |
| 2012/0316459 A1 | 12/2012 | Abreu |
| 2014/0128697 A1* | 5/2014 | Parfenova ............ A61B 5/4818 600/328 |

\* cited by examiner

ELECTRONIC HEADWEAR

FIELD OF THE INVENTION

The present invention relates generally to athletic headwear and, more particularly, headwear having a variety of physiological sensors, such as oxygen saturation, body temperature, pulse rate, and blood pressure.

BACKGROUND OF THE INVENTION

There has been an increasing interest in using devices and tools during exercise and athletic activities to enhance performance and also to monitor critical conditions. Measuring physiological characteristics during exercises can optimize workout routines. One such tool is an oximetry unit, which measures the oxygen saturation in blood and pulse rate. During intense exercise or at higher altitudes, there is a tendency for blood oxygen levels to drop. When the body is deprived of an adequate supply of oxygen, generalized hypoxia or tissue hypoxia may occur. Therefore, monitoring blood oxygen levels with an oximetry unit can be used to guide exercise, athletic training, and provide an alarm in critical conditions and situations.

Oximetry is a noninvasive assessment of arterial oxygen saturation (SpO2), which is the measurement of the amount of oxygen carried by hemoglobin in the blood stream. It relies on Beer-Lambert's law, which states that the concentration of an absorbing substance in a solution is related to the intensity of light transmitted through that solution. Accordingly, an oximetry unit uses small light-emitting diodes (LED) to transmit light and then measures the light not absorbed by the tissue by a photodetector to determine the concentration of oxygen in blood. An oximetry unit emits light of at least two different wavelengths, red (660 nm) and infrared (905, 910, 940 nm). Deoxyhemoglobin (hemoglobin not combined with oxygen) has a higher optical extinction in the red region of the light spectrum compared to oxyhemoglobin (hemoglobin that is combined with oxygen). In contrast, in the infrared region, the optical absorption of deoxyhemoglobin is lower than oxyhemoglobin. Thus based on the differences in light absorption, an oximetry unit can measure the amount of light absorbed to calculate the percentage of oxygen saturation in blood.

The oximetry sensor is usually placed on a thin part of the body such as a fingertip or an earlobe. Since oximetry sensors have been predominantly used for clinical or medical purposes, the site of the oximetry sensor placement has generally not been an issue because multiple satisfactory placement sites are readily available. However, during exercise or other athletic activities, traditional locations for oximetry sensor placement such as fingertip or earlobe can be problematic.

It should be appreciated that there remains a need for an assembly that easily measures physiological vital sign changes such as oxygen saturation, pulse, body temperature, and blood pressure of a user during physical exercise, athletic activities, and other critical situations. The present invention addresses this need and others.

SUMMARY OF THE INVENTION

Briefly, and in general terms, the invention provides an electronic headwear assembly, such as a self-contained electronic strap, that measures physiological changes, e.g., oxygen saturation, pulse, blood pressure, and body temperature of a user during physical exercise and other critical situations, as well as providing other functions and data, such as wireless communications (e.g., Bluetooth® and Wi-Fi transceivers), altitude, average speed, distance, time, number of calories burned, LED headlamp, mobile phone, radio/music player, USB port, and battery parameters, among others. The headwear assembly has multiple embodiments that encompass various types of headwear. Not only can the headwear assembly be used in a stand-alone headband, it can be placed inside the headband of a cap or visor, or in the lining of a helmet. The LED headlamp can be located approximately in the center of the outer front portion of the headwear, e.g., cap, visor, and headband.

In various embodiments in accordance with the invention, the headwear assembly can provide: integrated functionality with multitudes of functions of an external device such as a smart phone via wireless Bluetooth® or Wi-Fi transceivers (e.g., to announce, display, or record physiological data). The external device may have either wired or wireless connection for listening or corresponding to allow for two-way communication.

When placed in a headwear assembly, a preferred location for the oximetry sensor is in the front section and proximate to the forehead when worn. In an exemplary embodiment, the headwear assembly is a self-contained unit that is housed in a flexible material with a plurality of attachment means, such as hook-and-loop fasteners, for adjustability and attachment. In a headband embodiment, the headwear assembly can be rotated 180 degrees upside down for use on either the left or right side. The front of the headwear assembly can be marked to indicate the proper position of the oximetry sensor, so that the user can ensure that the oximetry sensor is in the appropriate location on the user's forehead. Moreover, the cap, visor, and headband embodiments can be rotated in a variety of ways that allow the sensors to remain in a proper location proximate to the skin without interference, and also with the speakers in proximity to the ears.

In an exemplary embodiment, the headwear assembly includes an oximetry sensor and a flexible circuit board assembly that is separately spaced apart from and electrically coupled to the oximetry sensor by a wire, flexstrip, or other means. More specifically, the oximetry sensor and circuit board assembly are confined in a flexible waterproof or water resistant casing.

In a detailed aspect of an exemplary embodiment, the present invention provides an oximetry sensor, having an LED and photodetector sensor, which measures percentage of oxygen saturation, and pulse rate.

In another detailed aspect of an exemplary embodiment, the circuit board assembly includes a LED driver circuit, a detector circuit, processor, and battery. The circuit board can further be defined to include a speaker or other sound/vibration generators or sensors including remote two-way devices, wired or wireless. In one aspect, the circuit board assembly is programmable to provide physiological data, such as body temperature, blood pressure, oxygen saturation, pulse and alarms for high and low levels, to the user through the speaker. In another aspect, audio prompts are announced periodically by way of the speaker to the user at preprogrammed levels.

In yet another detailed aspect of an exemplary embodiment, the circuit board assembly includes a wireless transceiver. In this manner, physiological data can be transmitted wirelessly to a recorder and display unit, such as a smart phone, that could be worn, for example, on the arm, wrist, and other part of the body.

Furthermore, in another exemplary embodiment, the circuit board assembly includes a control button accessible on the headwear body, the control button coupled to the processer. In one aspect, a user can manually press the control button to prompt the present invention to take a reading of the user's current physiological characteristics. Alternatively, the present invention is continuously measuring the user's physiological characteristics and manually pressing the button will provide data through audio announcements or visually through a display unit. Moreover, the central button can be activated from an external device whether connected by cable or wirelessly as previously described. Moreover, audio announcements can be initiated by voice activation commands.

For purposes of summarizing the invention and the advantages achieved or implemented over the prior art, certain advantages of the invention have been described herein. Of course, it is to be understood that not necessarily all such advantages may be achieved or implemented in accordance with any particular embodiment of the invention. Thus, for example, those skilled in the art will recognize that the invention may be embodied or carried out in a manner that achieves, optimizes, or implements one advantage or group of advantages as taught herein without necessarily achieving or implementing other advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment disclosed.

BRIEF DESCRIPTION OF THE DRAWINGS

Embodiments of the present invention will now be described, by way of example only, with reference to the following drawings in which:

FIG. 6b is a top view of the electronic assembly of the electronic strap of FIG. 6a.

FIG. 6c is a side view of the electronic assembly of the electronic strap of FIG. 6a.

FIG. 6d is a bottom view of the electronic assembly of the electronic strap of FIG. 6a.

DETAILED DESCRIPTION OF THE PREFERRED EMBODIMENTS

Figure 1A:
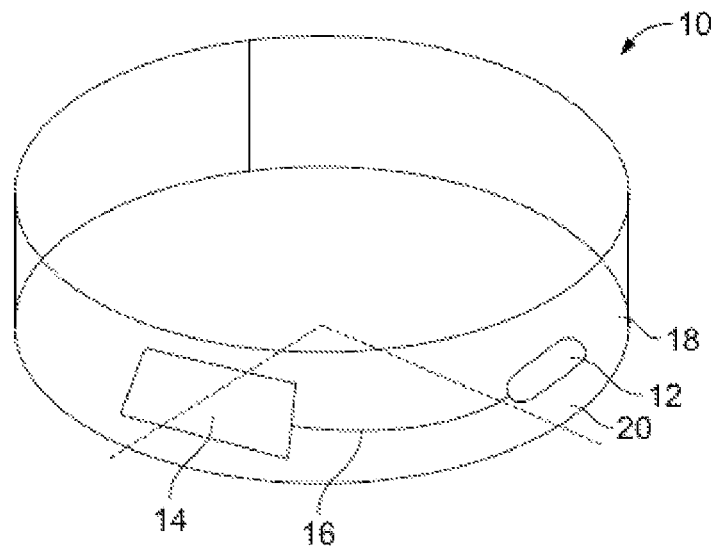
FIG. 1A is a perspective view of a headwear assembly in accordance with the present invention, depicting sensors and a circuit board assembly that are spaced apart and electrically coupled together.
Figure 1B:
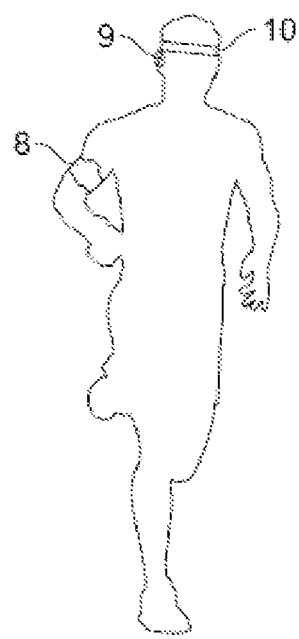
FIG. 1B is an elevational view depicting a user wearing the headwear assembly of FIG. 1, further wearing an smart phone housed in an armband and wireless earphones, the headwear assembly and smart phone wirelessly and operatively connected.
Figure 1C:
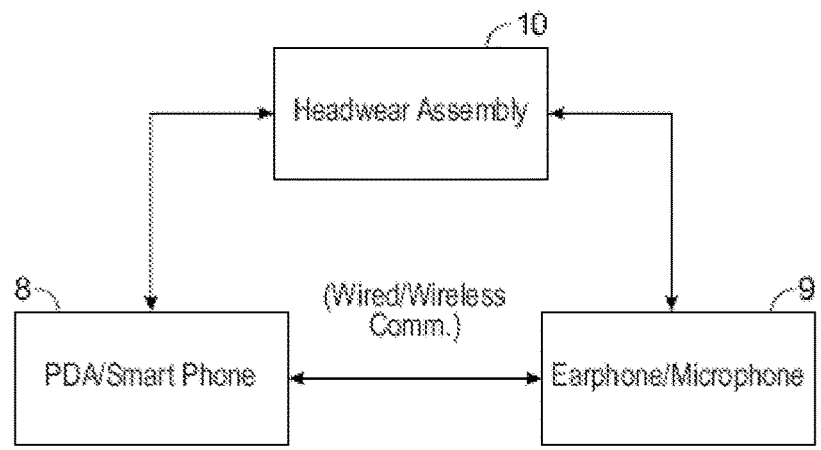
FIG. 1C is a simplified block diagram of the headwear assembly, smartphone, and earphones of FIG. 1B.

Referring now to the drawings, and particularly FIGS. 1A-1C, there is shown a headwear assembly 10 having an oximetry sensor (emitter/detector) 12 (This may include other sensors, such as temperature, blood pressure, etc.) and a circuit board assembly 14 that is spaced apart from and electrically coupled to the oximetry sensor (emitter/detector) by a wire/flexstrip 16, an air-tube, or other means. The headwear assembly 10 includes a headband 18. The oximetry emitter/detector 12 is located in a front section 20 of the headband, proximate to the forehead when worn. When the headwear assembly is worn, the oximetry sensor is positioned on one side of the user's lower forehead substantially above the eyebrows/eyes.

The position of the sensor 12 is advantageous for exercising or engaging in physical or other activities over both fingertip and earlobe oximetry sensor. Generally, for most physical activity, a headband is less obtrusive during exercise than an ear or finger sensor. Additionally, a person engaged in certain sports, such as tennis, cycling, running, or basketball, may be already accustomed to wearing headwear. Moreover, when compared to a fingertip oximetry sensor, a headband oximetry unit is advantageous, because it is a less active site during exercise. While the sensors are optimally located above the eyes, the electronic package may be conveniently and ergonomically located anywhere in the headband system including either side, back or front of the head.

Referring to the drawing in FIGS. 1B and 1C, the headwear assembly 10 will operate with external units, such as a PDA (personal data assistant), smart phone (8), and a headset or earphone microphone system (9). These may communicate either directly by wire/cable or by wireless means.

Due to the natural placement of a headband during exercise, the oximetry sensor 12 will be located optimally above the eyebrow. When properly worn in the preferred location, the LED emitter 22 and detector 24 (FIG. 2) of the oximetry sensor 12 lie above the eyebrow in the region of the most dense near surface blood flow.

In one embodiment, the headband 18 is made of a fabric that is wickable, stretchable, and breathable material, e.g., such as Dryline or spandex. The fabric can also be antimicrobial for odor control and stain resistant.

The user can rotate the headwear assembly 10 flipped upside down to have the oximetry sensor 12 located for use on either the left or right side of the user. The front 20 of the headband can be marked with the location of the sensor so the user can position the oximetry sensor in the appropriate location on the user's forehead.

The sensors 12 and circuit board 14 are confined in a flexible waterproof casing that is at least transparent in the region between the sensors 12 and the user's skin. In an exemplary embodiment, the sensors and circuit board are arcuate to conform comfortably to the user's forehead. Alternatively, the sensors and circuit board are encased in flexible material that will conform to the user's head when worn.

Furthermore, the wire (or air-tube) assembly 16 that connects the sensors and circuit board may include a waterproof or water resistant material or is confined in waterproof casing, and is flexible to conform to the user's head when the headwear assembly is worn.

Figure 2:
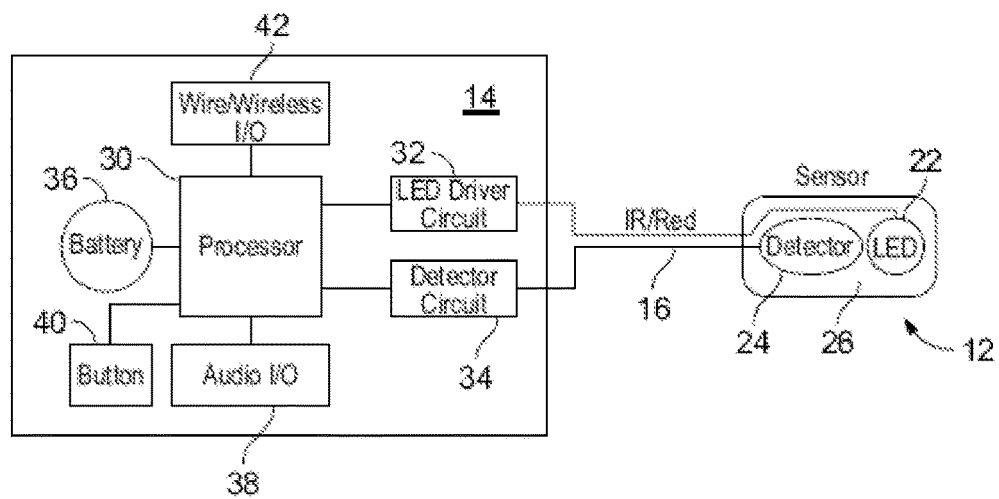
FIG. 2 is a simplified block diagram of the sensors and the circuit assembly of the headwear assembly of FIG. 1.

With reference to FIG. 2, the oximetry sensor 12 includes the emitter (LED) 22 and the detector 24 mounted to flexible, waterproof substrate 26. The LED and detector are placed adjacent to each other. The configuration of the sensor assembly is designed to minimize the amount of ambient light in the sensing area.

In the exemplary embodiment, the LED 22 emits at least two distinct wavelengths of light: red and infrared light. The detector is a photodetector capable of detecting the wavelengths of light emitted by the LED.

More particularly, The LED 24 emits light at two wavelengths (e.g., (1) 660 nm (red light); (2) 905, 910, or 940 nm (infrared light)). As light passes through tissue, oxyhemoglobin absorbs infrared light and allows red light to pass through, while deoxyhemoglobin does the opposite and absorbs red light but allows infrared light to pass through. Via the detector 24, the assembly measures the absorption ratio of the red and infrared light. The percentage of oxygen saturation is then calculated. To calculate the ratio of oxygen saturation, by a means known to those versed in the art, as blood pulses and fades with each heartbeat, the measurement of oxygen absorption from the peak level of the pulse is subtracted from the measurement of oxygen absorption at the lower level. In other embodiments, additional or alternative approaches can be used to measure pulse rate, e.g., such as utilizing blood pressure sensors as discussed herein below.

With continued reference to FIG. 2, the circuit board assembly 14 includes a processor 30, LED driver circuit 32, detector circuit 34, and battery 36. The circuit board assembly is connected to the sensor assembly 12. The processor 30 connects to the LED 22 through the LED driver circuit 32. After instructions to the LED 22 have been sent, the processor 30 receives the light absorption measurement data from the detector 24, through the detector circuit 34. The battery 36 powers the circuit assembly 14 and the sensors 12. The battery can be replaced. Alternatively, a rechargeable battery may be used. Charging of the battery may be via direct connection such as a USB connector or the LIKE or remotely using an inductive (magnetic) coupling method.

In a detailed aspect of an exemplary embodiment, the circuit board 14 contains memory that is coupled to the processor 14, making it programmable to provide customizable data to the user, which includes body temperature, oxygen saturation, pulse, blood pressure, and alarms for high or low levels and battery level. In another aspect, the headwear assembly can be programmed to announce periodic audio prompts by way of a speaker 38 at preprogrammed intervals or indirectly via an ear piece/microphone connection, either wired or wireless connected. Moreover, audio announcements can be initiated by voice activation commands.

In other embodiments, various other headwear configurations can be used. A speaker can be located proximate to an ear of the user, on either the left or right side, or both. Moreover, the cap, visor, and headband embodiments can be rotated in a variety of ways that allow the sensors to remain in a proper location proximate to the skin without interference, and also preferably, with the speakers in proximity to the ears.

In an exemplary embodiment, the circuit board assembly 14 further includes a button 40 and a wireless transceiver 42 such as Bluetooth®, Wi-Fi, or inductively coupled loop the like of which is used in many hearing aids. The button 40 is coupled to the processor 30 and powers the device on or off. In one aspect, the user can also press the button 40 to prompt the headwear assembly to take measurements. In another aspect, the user can press the button 40 to provide data through audio announcements using the speaker 38 or audibly/visually through a wireless transceiver 42 to a display unit such as a mobile phone or audibly through a listening device wired or wireless which is connected to an electronic device such as a mobile phone, such as shown in FIG. 1C.

Figure 3:
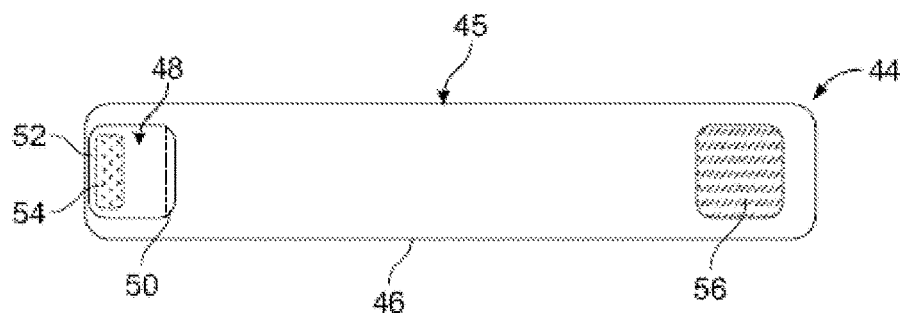
FIG. 3 is plan view of the headwear assembly of FIG. 1, depicting the front surface of the headband laid open, including an attachment tab for coupling opposing ends of the headband together.

With reference now to FIG. 3, a front surface 46 of another embodiment of a headwear assembly 44 is shown. The headwear assembly 44 includes a headband 45 having an attachment tab 48 having a proximal portion 50 coupled to the front surface and a free distal end 52. An attachment tab includes a first portion 54 of an attachment assembly that mates with a corresponding second portion 56 of the attachment assembly disposed on an opposing end of the headband. The attachment assembly can be any number of those known in the art, e.g., hook and loop, snaps, fasteners, and other means. The attachment tab 48 provides adjustable tension to securely attach to the user's head during exercise or athletic activities.

Figure 4:
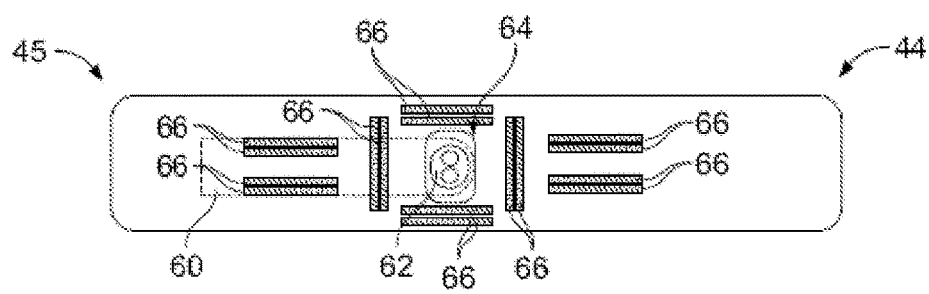
FIG. 4 is a plan view of a second embodiment of a headwear assembly in accordance with the invention, depicting an interior side of a headband, laid open, and an electronic strap having a sensing end exposed through an aperture of the headband.

With reference now to FIG. 4, there is shown an interior side of a headwear assembly 44, laid open, including an electronic strap 60 having a sensing end 62 exposed through an aperture (e.g., transparent window) 64 the headband 45. The interior side of the headband includes several slip-resistant bands 66 disposed about the aperture to maintain the position and minimize exposure to ambient light of the sensing end, thereby maintaining the accuracy of readings. The slip-resistant band can be formed of polymeric material secured to the interior side. The slip resistance bands ideally should be interrupted rather than a single continuous band to give the best immobilization effect possible even in moisture environments because movement of any particular single band will not affect movement in any of the others.

Figure 5:
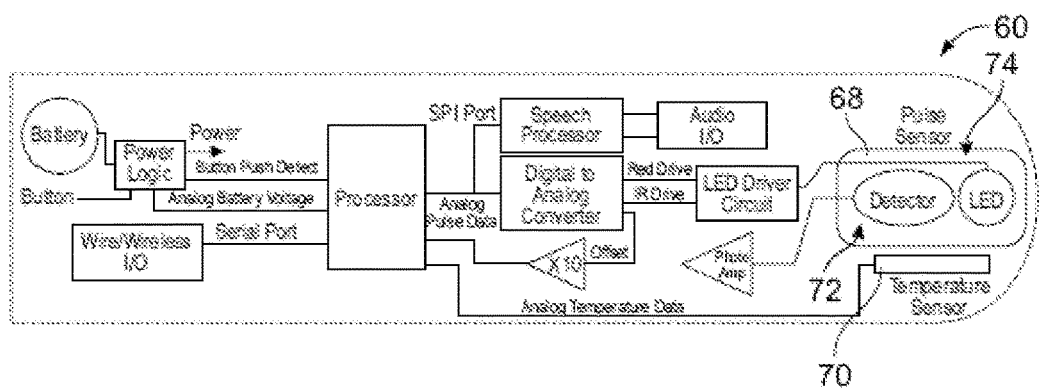
FIG. 5 is a simplified block diagram view of the electronic strap of FIG. 4.

With reference now to FIG. 5, the electronic strap 60 includes a circuit board that house all components, including a pulse and oxygen saturation sensor 68 and a temperature sensor 70 at the sensing end. The pulse sensor includes a detector 72 and an LED 74. The pulse sensor is connected to an LED driver circuit, which communicates with a processor via a digital to analog convertor (D/A convertor). The detector communicates with the processor via a photo amplifier. The body temperature is obtained by a temperature sensor (e.g., thermistor), which is located adjacent to the sensor 68. The electronic strap further includes a speaker, a transducer, and a speaker processor that enables the strap to announce measurements to the wearer. The electronic strap can communicate bi-directionally with other devices via wireless communications, e.g., Bluetooth®, WI-FI, or inductive means. The microphone and related processor enable the strap to receive and process verbal commands from the user.

With reference now to FIGS. 6*a*-6*d*, an electronic strap 59 is shown, configured to facilitate comfort and flexibility when worn against the head with the sensing end positioned to be disposed in an appropriate location for accurate measurements when worn. Components are distributed about the several circuit boards connected via bridge connections (e.g., flex wire, thin bridge of circuit board).

Figure 6A:
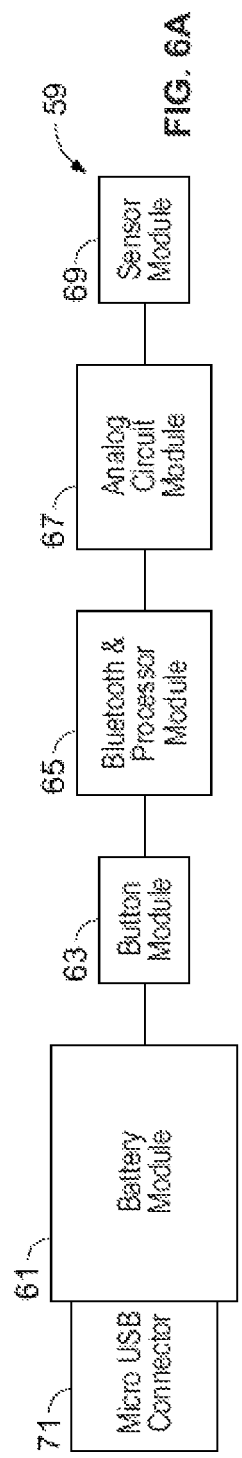
FIG. 6a is a simplified block diagram of an electronic strap in accordance with the invention.
Figure 6B:
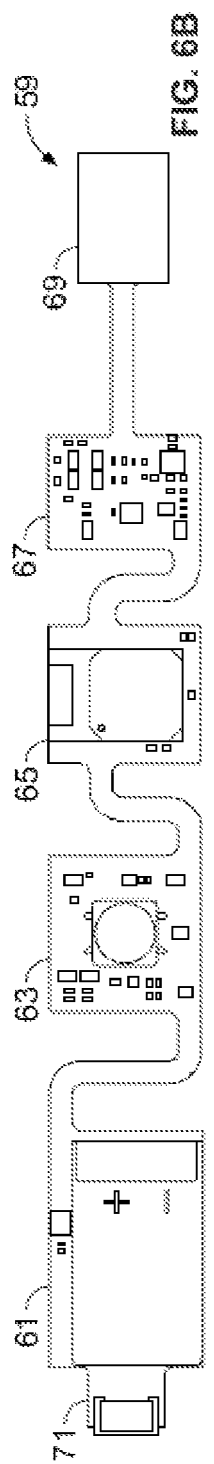
Figure 6C:
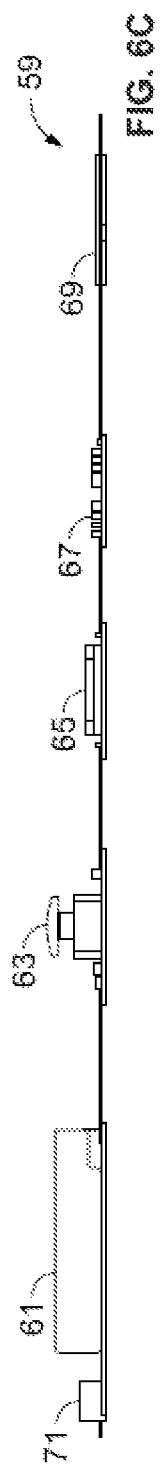
Figure 6D:
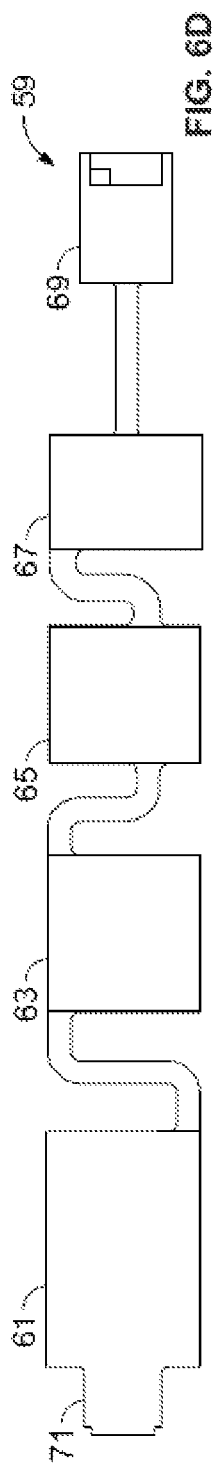
Figure 7:
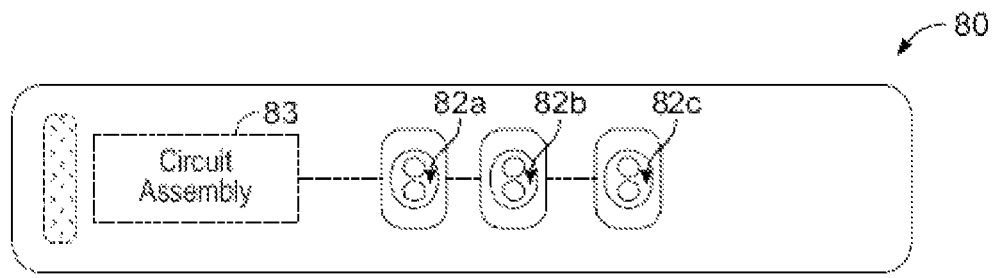
FIG. 7 is a plan view of a third embodiment of a headwear assembly in accordance with the invention, depicting an interior side of a headband, laid open, having multiple sensing sections exposed through apertures of the headband.

As best seen in FIG. 6*a*, the electronic strap 60 includes a battery module 61, button module 63, communications (e.g., Bluetooth®, WIFI) and processor module 65, analog circuit module (analog) 67, and a sensor module 69. A USB connector 71 is disposed adjacent and operatively coupled to the battery module.

With reference now to FIGS. 7 to 10, the headwear assembly 80 can include a plurality of sensors 82(*a,b,c*) for oximetry and/or for blood pressure (e.g., 90 of FIG. 12), in which such sensors are disposed in spaced relationship in prescribed locations about the headwear assembly to measure various selected locations on the user, when worn. The advantage of multiple sensors is that the unit can obtain the strongest and most accurate reading from multiple readings.

Figure 8:
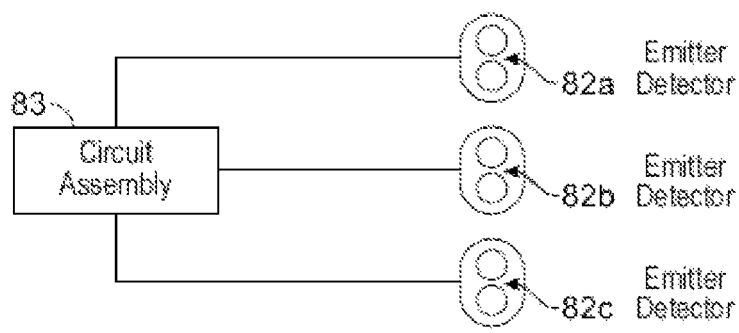
FIG. 8 is a simplified block diagram view of the sensors and the circuit assembly of the headwear assembly of FIG. 7.

With reference now to FIG. 8, multiple sensors may be electronically or optically connected back to the circuit assembly 83. When optically connected the emitter/sensor units 82(*a,b,c*) may be included with the circuit assembly and optical wave-guides used to transfer the sensing light to and from the monitoring point. The plurality of sensors may be connected to the processing unit individually, multiplexed, or aggregated to a sensor block or a combination of all three means.

Figure 9:
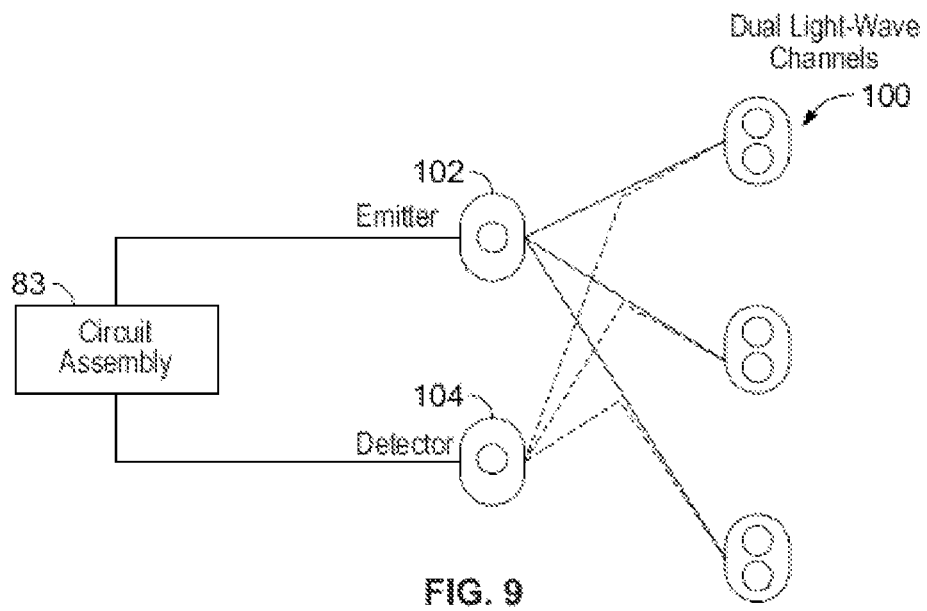
FIG. 9 is a simplified block diagram view of sensors and the circuit assembly of another embodiment of a headwear assembly in accordance with the invention.
Figure 10:
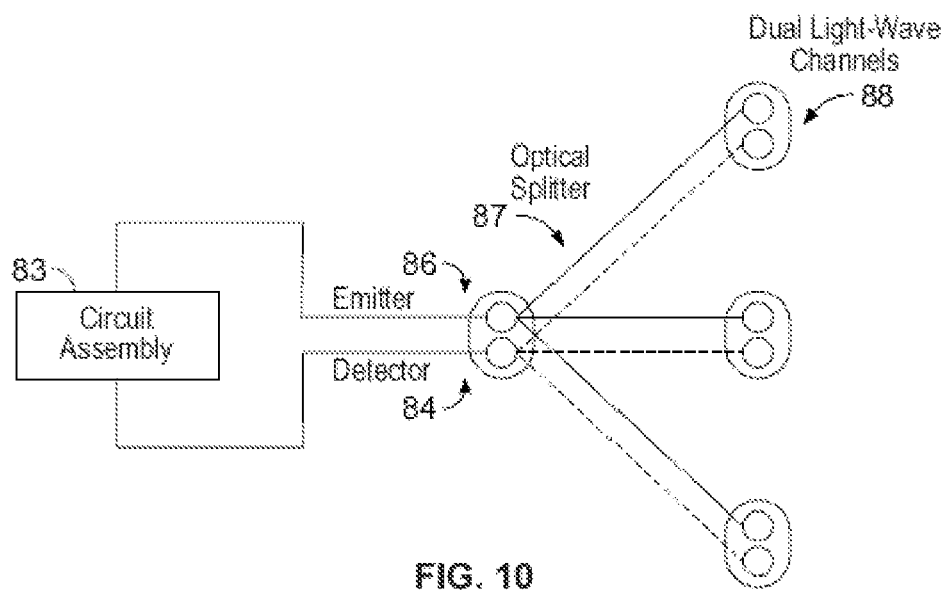
FIG. 10 is a simplified block diagram view of sensors and the circuit assembly of another embodiment of a headwear assembly in accordance with the invention.
Figure 11A:
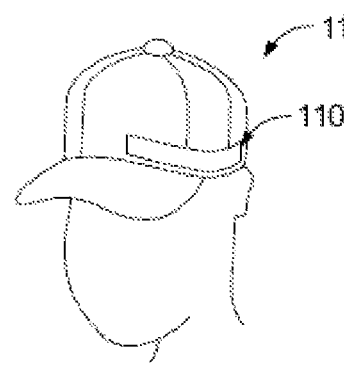
FIGS. 11a-11d are perspective views of an electronic strap disposed in various headwear assemblies in accordance with the invention.
Figure 11B:
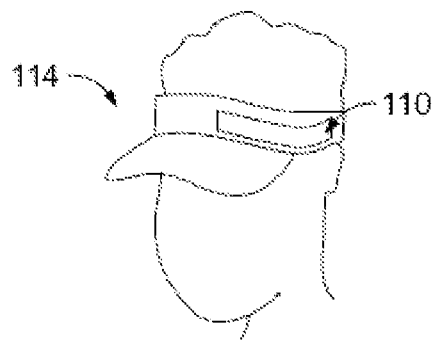
Figure 11C:
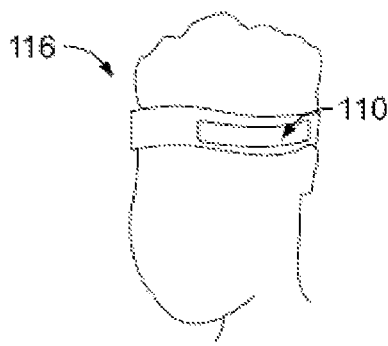
Figure 11D:
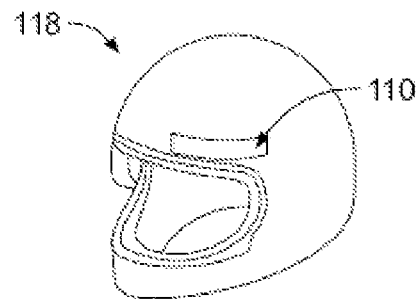

In the embodiments of FIGS. 9 and 10, the oximetry sensors include channels for directing light, e.g., lightwave guides or fiber optics 100, that are positioned to direct light to the measuring location on the user. In this manner, other components of the sensor can be spaced apart from the measuring location. For example, components of the oximetry sensor can be mounted on the circuit board along or in conjunction with use of light wave guides or optical fibers for skin contact. An advantage of the multiple light wave fibers over multiple sensors is that only one sensor pair (emitter 102 and detector 104) is needed and the smaller multiple light wave fibers can allow for more sensor data collection in a limited space. FIG. 9 provides for optical aggregation between the multiple sensors to a single detector 104 and emitter 102 and the multiple sensor points. Separate fibers may be used for the emitter path and the sensor path. FIG. 10 shows that alternately a single fiber/wave guide may be used from each sensor point and a suitable optical splitter 87 used to isolate the electronic emitter and detector/sensor paths.

With reference now to FIGS. 11*a*-11*d*, exemplary embodiments are shown in which an electronic strap 110 is installed in various types of headwear, such as a cap 112, visor 114, a headband assembly 116, and a helmet 118. In the helmet-lining embodiment 118, a properly fit helmet will ensure proper tension of the electronic strap to the head. Additionally, in one area of a headband version, a strap, with an adjustable end, such as Velcro or other means, is placed on the exterior surface of the headband. This may allow for adjustment to the tension of the headband on the head of the user and will allow for fitting to a smaller head size. Maintaining proper tension of the headband on the head avoids measurement inaccuracies, such as venous pulsation interference with inadequate tension or compromised blood flow with excess tension.

Figure 12:
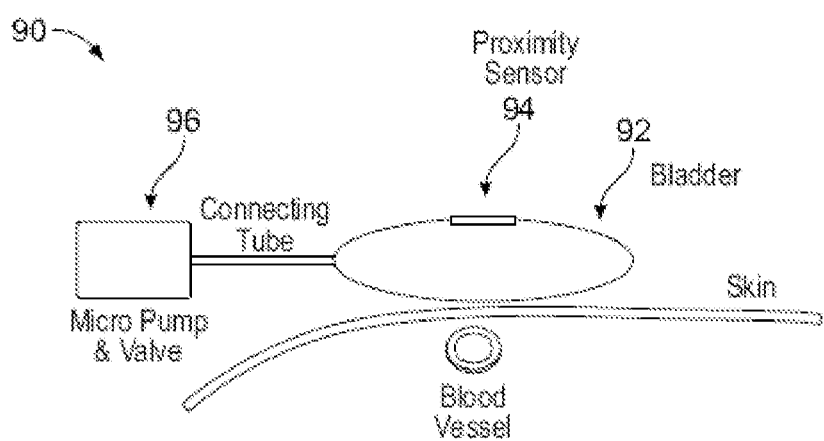
FIG. 12 is a cross-sectional view of a blood pressure sensor for use in selected embodiments of a headwear assembly in accordance with the invention.

With reference now to FIG. 12, a blood pressure monitor 90 is disposed in a headwear assembly (e.g., 10, 44) in accordance with the present invention. The blood pressure monitor includes a pressurized bladder 92 disposed over a blood vessel of the user. Preferably, a blood vessel is near the surface of the user's skin, such as blood vessels in the temporal region of the scalp, such as the superficial temporal artery. A proximity sensor 94 is coupled to the bladder. In this arrangement, the volumetric change of the vessel is transferred to the bladder such that this volumetric change can be sensed by the sensor. Additionally, the bladder may be inflated and deflated using a small air pump 96 and bleed off valve.

Examples of effective sensors 94 include capacitive proximity sensors, e.g., which can translate displacement to an analog of the capacitance such as a voltage or digital count. Another example is a resistive band around the bladder, e.g., to translate circumference to resistance in a proportional manner. A pressure sensor can be attached to the bladder to measure pressure changes therein. An air pump 96 can be used to restrict the blood flow, periodically, to measure blood pressure, in a sphygmomanometer-type configuration.

Blood pressure monitor 90 can be located over a temporal region of the scalp or other area. Blood pressure sensor can include proximity sensors combined with small bladders to record volume displacement or capacitance sensors or stretch transducers to record displacement by way of voltage or resistance measurements, to measure the blood pressure of the user. The blood pressure monitor can be mounted on the substrate of the electronic strap (e.g., 60, 12, 14) and electronically coupled to the circuit board by a flexwire or other means. Multiple blood pressure monitors can be disposed strategically about the headwear assembly, to improve reliability by obtaining the strongest and most accurate reading from multiple measurements.

It should be appreciated from the foregoing that the present invention provides an exercise or athletic headwear assembly that measures physiological changes of a user during physical exercise, athletic activities, or other situations including medical monitoring through the use of sensors. Through the natural placement of a variety of headwear embodiments, the sensors will be placed in the preferred location on a user's head. The sensors measure the oxygen saturation, blood pressure, and pulse rate of a user. A thermistor can also be included to measure body temperature. The headwear assembly is capable of presenting data to the user through audio means as well as wireless transmission to other devices, such as a smart phone, where it can be presented to the user by display or audio means on the device itself or through a wired or wireless listening device.

Although the invention has been disclosed in detail with reference only to the exemplary embodiments, those skilled in the art will appreciate that various other embodiments can be provided without departing from the scope of the invention. Accordingly, the invention is defined by the claims set forth below.

What is claimed is:

1. An oximetry headwear assembly, comprising:
   a headwear body having a front portion disposed proximate to the forehead when worn;
   a waterproof casing attached to the headwear body;

an oximetry sensor having an emitter and a detector disposed in the front portion of the headwear body, the oximetry sensor confined within the waterproof casing;
a thermistor mounted adjacent to the oximetry sensor, the thermistor confined within the waterproof casing; and
a circuit board assembly having a processor, the circuit board assembly confined within the waterproof casing and electrically coupled to the oximetry sensor and the thermistor, the oximetry sensor and the circuit board assembly are configured to measure oxygen saturation and pulse rate of the user, the thermistor and the circuit board assembly are configured to measure the body temperature of the user.

2. The headwear assembly as defined in claim 1, wherein the oximetry sensor is confined within the headwear body, and the headwear body provides an aperture in the front portion such that the oximetry sensor is aligned with the aperture proximate to the forehead, and the waterproof casing is transparent in the region between the emitter and the detector and the user's skin, when worn.

3. The headwear assembly as defined in claim 1, further comprising a plurality of slip-resistant, light barrier bands disposed in a circumscribing manner about the oximetry sensor to block ambient light and to maintain positioning of the oximetry sensor on the forehead, when worn.

4. The headwear assembly of claim 3, wherein the circuit board assembly, oximetry sensor and thermistor are disposed on an integrally formed substrate, the oximetry sensor and thermistor are disposed on a proximal end of the substrate, the circuit board assembly having a LED driver circuit, the processor, and a battery aligned in a proximal to distal manner across the substrate.

5. The headwear assembly as defined in claim 1, wherein the circuit board assembly and the oximetry sensor are disposed on an integrally formed substrate.

6. The headwear assembly as defined in claim 5, wherein the circuit board assembly includes an LED driver electrically coupled to the emitter and a detector circuit operatively coupled to the detector, both the LED driver circuit and detector circuit are operatively coupled to the processor, and the circuit board assembly further includes wireless transceiver operatively coupled to the processor.

7. The headwear assembly as defined in claim 5, wherein the circuit board assembly includes a control button accessible along a side of the headwear body, the control button coupled to a processor.

8. The headwear assembly as defined in claim 1, further comprising a plurality of circuit boards connected to each other in series via bridge connections, wherein the plurality of circuit boards are arranged in a linear manner, and each of the plurality of circuit boards contain an electronic component.

9. The headwear assembly as defined in claim 1, the headwear body is configured as a headband to be worn about the head of a user, formed of wicking, stretchable fabric, the body includes an adjustable end having hook-and-loop attachment to maintain tension, when worn.

10. The headwear assembly of claim 1, wherein the oximetry sensor and the circuit board assembly are confined within the waterproof casing, the circuit board assembly further having a rechargeable battery that is recharged by inductive coupling.

11. An oximetry headwear assembly, comprising:
a headwear body having a front portion disposed proximate to the forehead when worn;
an oximetry sensor having an emitter and a detector disposed in the front portion of the headwear body;
a thermistor mounted adjacent to the oximetry sensor;
a circuit board assembly secured to the headwear body and electrically coupled to the oximetry sensor and the thermistor, the oximetry sensor and the circuit board assembly are configured to measure oxygen saturation and pulse rate of the user, the thermistor and the circuit board assembly are configured to measure the body temperature of the user, the circuit board assembly including a processor; and
a plurality of slip-resistant, light barrier bands disposed in a circumscribing manner about the oximetry sensor to block ambient light and to maintain positioning of the oximetry sensor on the forehead, when worn.

12. The headwear assembly as defined in claim 11, wherein the circuit board assembly includes an LED driver electrically coupled to the emitter and a detector circuit operatively coupled to the detector, both the LED driver circuit and detector circuit are operatively coupled to the processor, and the circuit board assembly further includes wireless transceiver operatively coupled to the processor.

13. The headwear assembly as defined in claim 11, wherein the circuit board assembly and the oximetry sensor are disposed on an integrally formed substrate.

14. The headwear assembly as defined in claim 11, wherein the plurality of slip-resistant, light barrier bands directly contact the skin of the user, when worn.

15. A headwear assembly, comprising:
a headband configured to circumscribe the head of a user when worn, the headband having front portion disposed proximate to the forehead when worn;
an oximetry sensor having a flexible, waterproof substrate, an emitter mounted to the substrate proximate to a distal end of the substrate, and a detector mounted to the substrate proximate to a proximal end of the substrate, the oximetry sensor disposed in the front portion of the headband such that the oximetry sensor is proximate to forehead of a user, when worn;
a thermistor mounted adjacent to the oximetry sensor;
a circuit board assembly, including a processor, disposed in the headwear body spaced apart from and electrically coupled to the oximetry sensor and the thermistor, the oximetry sensor and the circuit board assembly are configured to measure oxygen saturation and pulse rate of the user, the thermistor and the circuit board assembly are configured to measure the body temperature of the user; and
a plurality of slip-resistant, light barrier bands disposed in a circumscribing manner about the oximetry sensor to block ambient light and to maintain positioning of the oximetry sensor on the forehead, when worn, wherein the plurality of slip-resistant, light barrier bands directly contact the skin of the user when worn.

16. The headwear assembly as defined in claim 15, comprising a plurality of sensors for oximetry and/or for blood pressure disposed in spaced relationship in prescribed locations to measure various selected locations on the user, when worn.

17. The headwear assembly as defined in claim 15, wherein the circuit board assembly is encased in waterproof material.

18. The headwear assembly as defined in claim 17, wherein the oximetry sensor and thermistor are encased in waterproof material.

* * * * *